United States Patent [19]

Rizzardo et al.

[11] Patent Number: 5,665,839

[45] Date of Patent: Sep. 9, 1997

[54] RING OPENING MONOMERS

[75] Inventors: Ezio Rizzardo, Wheelers Hill; Richard Alexander Evans, Clayton; Graeme Moad, Kallista Victoria; San Hoa Thang, Clayton South, all of Australia

[73] Assignee: Commonwealth Scientific and Industrial Research Organisation, Campbell, Australia

[21] Appl. No.: 464,701

[22] PCT Filed: Dec. 21, 1993

[86] PCT No.: PCT/AU93/00667

§ 371 Date: Jul. 20, 1995

§ 102(e) Date: Jul. 20, 1995

[87] PCT Pub. No.: WO94/14792

PCT Pub. Date: Jul. 7, 1994

[30] Foreign Application Priority Data

Dec. 22, 1992 [AU] Australia ............... PL6516/92
Jan. 5, 1993 [AU] Australia ............... PL6661/93

[51] Int. Cl.[6] .................. C08F 228/06; C08F 224/00; C08F 220/10; C08F 220/44; C08F 212/08; C07D 327/02; C07D 327/10

[52] U.S. Cl. .................. 526/257; 549/10; 549/267; 549/271; 526/328.5; 526/342; 526/347; 526/266

[58] Field of Search .................. 549/11, 10, 14, 549/267, 271; 526/257, 266, 328.5, 342, 347

[56] References Cited

U.S. PATENT DOCUMENTS 4,889,938  12/1989  Kristen et al. ............... 549/10

FOREIGN PATENT DOCUMENTS 42-005433  3/1967  Japan.

Primary Examiner—Joseph L. Schofer
Assistant Examiner—Wu C. Cheng
Attorney, Agent, or Firm—Bacon & Thomas

[57] ABSTRACT

Compound of the Formula 1

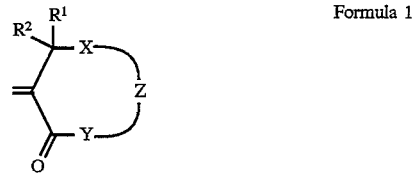

Formula 1 wherein:

$R^1$ and $R^2$ are independently selected from the group comprising hydrogen, $C_1$ to $C_6$ alkyl, $C_1$ to $C_6$ haloalkyl, phenyl, and substituted phenyl;

X is selected from the group comprising sulfur, sulphone, disulfide;

Y is selected from oxygen, carbon, N—H, N-alkyl, N-aryl, or sulfur; and

Z is any linking functionality.

The compounds represent a new class of ring opening monomers.

9 Claims, No Drawings

RING OPENING MONOMERS

This invention relates to a new class of ring opening monomers, that is unsaturated organic compounds which when used as monomers undergo ring opening on free radical polymerisation. Ring opening monomers are important in minimising volume shrinkage during polymerisation. Additionally, ring opening monomers are useful in providing an alternative method of incorporating functionalities such as amide, ester or carbonate into the backbone of a polymer. Conventionally, such functionalities are introduced by step growth polymerisation (i.e. polyesterification) rather than chain growth polymerisation (i.e. free radical). The limitations of step growth polymerisation are that (a) very high conversion is required for high molecular weight polymer and (b) elimination products (such as water or HCl) are formed and require removal. In contrast, chain growth polymerisation (free radical or ionic) results in very high molecular weight polymer from the beginning of the polymerisation with no elimination products generally being formed.

There are many types of ring opening monomers available for cationic or anionic polymerisation. However, there are only a limited number of ring opening monomers available for free radical polymerisation. A review by Endo et al. in Chapter Five of *New Methods for Polymer Synthesis*, Plenum Press, New York 1992, summarises the present state of the art. The major types of free radically polymerizable, ring opening monomers are vinyl cyclopropanes, various cyclic vinyl ethers, cyclic ketene acetals (U.S. Pat. No. 4,857,620 to PPG Industries, Inc.), spiro ortho esters and spiro ortho carbonates. These, however, suffer from limitations. Ring opening of vinyl cyclopropanes is a reversible process and substituents that favour ring opening may also inhibit polymer growth by excessive stabilisation of the ring-opened propagating radical. The oxygenated monomers listed above generally are extremely sensitive to trace mounts of acid. This makes their synthesis and subsequent storage difficult. Furthermore ring opening is not guaranteed and the final polymers can contain various proportions of opened and unopened rings. In addition, the spiro ortho esters and spiro ortho carbonates have the following disadvantages:

(i) They are sensitive to impurities. Impurities can prevent ring opening from occurring. This can make the polymerisation somewhat irreproducible.

(ii) They have low reactivity towards free radical polymerisation.

(iii) They have low reactivity ratio with common commercial vinyl monomers such as styrene and methyl methacrylate (and monomers of similar reactivity).

(iv) They are crystalline compounds with low solubilities in organic solvents and monomers. The book *Expanding Monomers*, Eds. Sadhir, R. K. and Luck, R. M. CRC Press, Boca Raton, 1992, details the chemistry and use of spiro ortho esters and carbonates.

The present invention provides a new class of organic compound that undergoes ring opening by free radical polymerisation. These compounds are readily soluble in common organic solvents and monomers. They are stable to acidic and basic conditions, and are easily handled with no special precautions required. Because they contain an acrylate skeleton, they can readily copolymerise with the major commercial monomers of similar reactivity such as acrylates, methacrylates, acrylonitrile, methacrylonitrile, styrenes and related monomers.

Accordingly the present invention provides compounds of the Formula 1

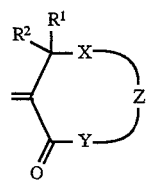

Formula 1 wherein:

$R^1$ and $R^2$ are independently selected from the group comprising hydrogen, $C_1$ to $C_6$ alkyl, $C_1$ to $C_6$ haloalkyl, phenyl, and substituted phenyl;

X is selected from the group comprising sulfur, sulphone, disulfide;

Y is selected from oxygen, carbon, N—H, N-alkyl, N-aryl, or sulfur; and

Z is any linking functionality.

Preferably X is S and Y is O.

Suitable linking functionalities for Z are —$(CWT)_n$—, —O—(CO)—O—$(CWT)_m$—, —$(CWT)_n$—, —$(CWT)_n$—O—(CO)—$(CWT)_m$—, —$(CWT)_n$—O—$(CWT)_m$—, —$(CWT)_n$—CO—$(CWT)_m$—, —$(CWT)_n$—(C=O)—, —$(CWT)_n$—S—$(CWT)_m$—, —$(CWT)_n$—S—S—$(CWT)_m$—, —$(CWTCWT)_n$—, phenylene, or substituted phenylene (where W, T are independently selected from hydrogen, $C_1$ to $C_6$ alkyl, $C_1$ to $C_6$ haloalkyl, phenyl, substituted phenyl or halogen and m,n are whole numbers). The ring system in Formula 1, preferably contains from six to 50 atom.

In this specification "substituted" group means that a group may be substituted with one or more groups selected from: alkyl, alkenyl, alkynyl, aryl, halo, haloalkyl, haloalkenyl, haloalkynyl, haloaryl, alkoxy, alkenyloxy, aryloxy, haloalkoxy, haloalkenyloxy, haloaryloxy, amino, alkylamino, arylamino, acyl, aroyl, arylacyl, acylamino, alkylsulphonyloxy, arylsulphenyloxy, heterocyclyl, heterocycyloxy, heterocycylamino, haloheterocyclyl, alkoxycarbonyl, alkylthio, alkylsulphonyl, arylthio, arylsulphonyl, aminosulphonyl, dialkylamino and dialkylsulphonyl.

The compounds of the invention may be polymerised or copolymerised by any of the methods known in the art.

Accordingly, in another aspect this invention provides a polymerisation process which comprises free radical polymerisation of a compound of Formula 1 optionally in the presence of one or more comonomers.

When undergoing polymerisation, the compounds of this invention ring open by undergoing beta bond cleavage in the manner illustrated below in Scheme 1 for the compound with $R^1=R^2=H$; X=S; Z=—$CH_2CH_2$—; Y=O.

Scheme 1

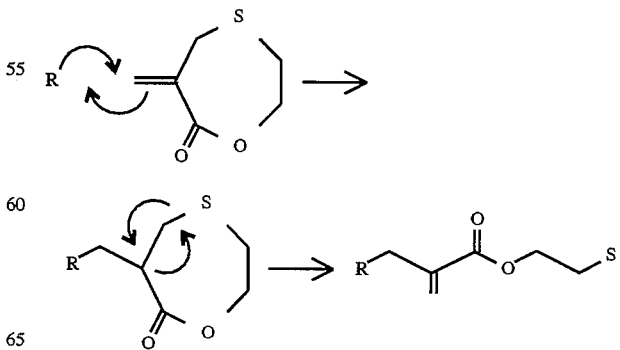

Generally, the polymers and copolymers resulting from the polymerisation of Formula 1 will contain the following structure (Formula 2) as the repeating unit.

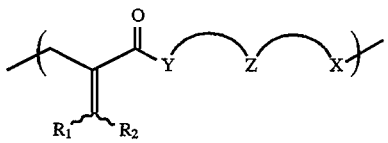

Formula 2

The polymerisation process of the invention is applicable to the manufacture of polymers requiring functionality such as ester, amide or thioester functionality in the polymer backbone and not simply as group attached to the backbone. Typically, in the prior art such polymers must be made by step growth polymerisation which requires that the polymerisation be taken to very high conversion in order to get high molecular weights. By using the compounds of the present invention in free radical polymerisation as comonomers in copolymerisations polymers may be made with controlled mounts of the repeating unit of Formula 2.

In a further aspect, this invention provides novel polymers made by the polymerisation process of the invention.

The compounds of the invention enable the production of a variety of polymers with structures not otherwise obtainable. The presence of an acrylate group in a polymer formed by free radical polymerisation is novel and allows a wide scope for further processing of the polymer. As a specific example, the activated methylene group can be used as a point of further chemical manipulation. Such a manipulation can be in the form of standard addition chemistry to the alpha-beta unsaturated skeleton or it can comprise using the active methylene unit as a point of grafting or crosslinking.

This crosslinking (for compounds where $R^1 50$ $R^2$=H) can occur during copolymerisation, e.g. with styrene as the comonomer, or alternatively, the crosslinking can be performed on the final copolymer as a separate step.

The compounds of the invention may be utilised to minimize shrinkage during polymerisation because of their ability to ring open. Such suppression of volume shrinkage can find application in polymeric coatings, adhesives, dental restorative materials, matrix resins for composites, and the fabrication of optical lenses. Other potential uses which involve incorporating the structure of Formula 2 into polymers include the creation of (i) degradable polymers, (ii) routes to α,ω-functionalised polymers, (iii) modifiers of refractive indices in optical lenses based on monomers of comparable reactivities to acrylates and styrenes, and iv) modification of physical properties of a polymer.

Compounds of Formula 1 can be prepared from commercially available starting materials.

The compounds of Formula 1 can be used as comonomers where they undergo complete ring opening or they may be homopolymerised to give a homopolymer which may contain a proportion of unopened rings (for compounds where $R^1$=$R^2$=H). The polymerisation maybe carried out in bulk or solution. Because they contain an acrylate skeleton, the compounds of this invention have reactivities similar to acrylates. This means they can readily polymerise with any appropriate monomers which copolymerise with acrylates. Such monomers include other acrylates, methacrylates, acrylonitriles, methacrylonitriles, and styrenes. The Polymer Handbook (ed Brandup) contains lists of reactivity ratios of monomers and its consultation will provide those skilled in the art other monomers of suitable reactivity.

When $R^1$=$R^2$=H, the compounds of Formula 1 will copolymerise with appropriate 1,1-disubstituted ethylene monomers, e.g. methyl methacrylate (MMA) and methylacrylonitrile (MAN) to give soluble polymers (provided the compound of Formula 1 is in lower concentration than the chosen comonomer) with complete ring opening occuring.

However, in copolymerisations with appropriate monosubstituted monomers (e.g. styrene) or in homopolymerisations, crosslinking may readily occur to give insoluble polymers. When the alpha position is substituted (e.g. $R^1$=H, $R^2$=$CH_3$, i.e. compound 6 below), homo- and co-polymerisation with other monosubstituted monomers (e.g. styrene) can occur without crosslinking to give soluble polymers.

From numerous experiments involving copolymerisations of compounds 1–4 (below) with MMA, it is apparent that the reactivity ratios of MMA and the compounds are about 1. That is to say that the composition of the monomer feed will give a copolymer of the same composition. The benefit of this is self evident.

For copolymerisations involving compounds with an alpha substitutent(s) the reactivity of the compounds are slightly lower. For example, for compound 6 ($R^1$=H, $R^2$=$CH_3$), (through the use of the integrated form of the copolymerisation equation), it was determined that $r_1$(MMA)=2.05±0.06 and r2 (comp.6)=0.48±0.03. Thus, useful amounts of incorporation of the ring opening monomer in the final copolymer is still readily achievable with suppression of crosslinking.

Examples of preferred compounds of Formula 1 are the compounds 1–6 shown below.

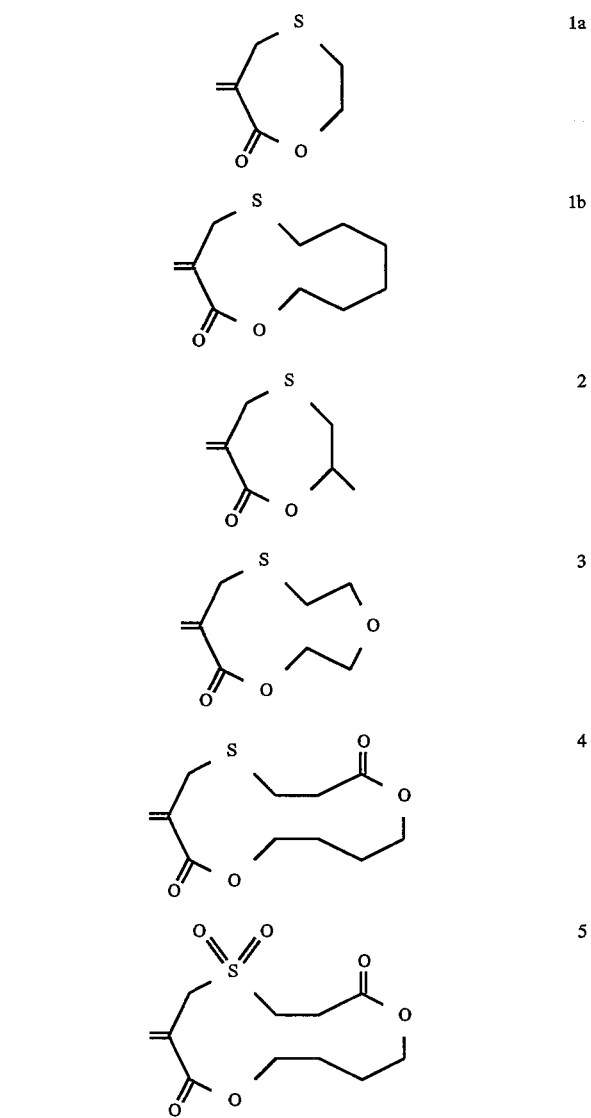

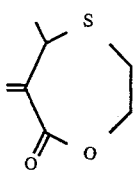

The methods of production of the compounds of formula 1 are illustrated by the following examples:

General Procedure for the Preparation of the Lactone Subclass of Compounds of Formula 1.

The compounds 1–6 above are lactones of medium ring size. They are prepared from the corresponding ring opened hydroxy acids. To achieve internal esterification rather than simply polyesterification, special conditions and reagents are generally required. Firstly, the technique of high dilution is advantageous. Thus, the appropriate hydroxy acid should be added very slowly (over a number of hours) to a large volume of solvent containing a cyclisation catalyst or reagent. This greatly favours lactonisation over other intermolecular reactions such as polyesterification. Secondly, when using the high dilution technique, either the hydroxy or acid group on the molecule being cyclised should preferably be activated to encourage attack by the other group. There are a number of methods in the literature that can be used, examples are the Corey Method, the Masamune Method, the Mitsunobu Method and the Mukaiyama method. The method used in the following examples is the Mukaiyama method using the "Mukaiyama" reagent, 2-chloro-1-methylpyridinium iodide. This method activates the acid group to attack by the hydroxy group. It will be apparent to the reader that the other methods or synthetic routes might be used with equal success. For example, the compounds might be synthesised via chloropyruvates with a final step using the Wittig reaction to convert the alpha-carbonyl into the required methylene group.

The preparation of the compounds of the invention and their use in preparing polymers is further illustrated by the following non-limiting examples.

EXAMPLE 1

Preparation of 6-methylene-1,4-oxathiepan-7-one (1a).

A solution of 5 g (0.031 moles) of α-(((2-hydroxyethyl)thio)methyl)acrylic acid and 35 ml (25 g, 0.25 moles, 8 molar equivalents) of triethylamine in 50 ml of dry dichloromethane was added by a mechanically driven syringe pump to a refluxing solution of 550 ml of dry dichloromethane containing 31.5 g (0.123 moles, 4 molar equivalents) of 2-chloro-1-methylpyridinium iodide over seven hours.

After all of the α-(((2-hydroxyethyl)thio)methyl)acrylic acid solution had been added, the solution was further refluxed for 40 minutes. The solution was filtered and the filtrate evaporated to give a viscous slurry. The slurry was taken up in water and extracted with dichloromethane (3×100 ml). The extracts were dried, evaporated to give 6.8 g of orange oil. The oil was chromatographed on silica using dichloromethane as eluent to give 3.08 g (69% yield) of a clear oil.

$^1$H NMR (CDCl$_3$) δ2.95 (2H, mult.), 3.36 (2H, s, allylic CH$_2$), 4.50 (2H, mult., —OCH$_2$—), 5.60 (1H, s, vinylic), 5.85 (1H, s, vinylic).

$^{13}$C NMR (CDCl$_3$) δ30.1 & 30.9 both (—S—CH$_2$—), 69.3 (—O—CH$_2$—), 124.8 (=CH$_2$), 142.0 (quat. =C), 171.0 (C=O).

Mass spectrum (E.I.) m/z 144 (M$^+$, 100), 116 (60), 86 (45), 68 (95).

IR spectrum (thin film, CCl$_4$) 2939 w, 1727 vs, 1454 w, 1414 m, 1312 s, 1285 m, 1235 w, 1200 w, 1140 s, 1060 s sh, 1021 m, 941 m cm$^{-1}$.

$n_D^{20}$=1.547–9

$d^{25}$=1.279 g/cc

EXAMPLE 2

Preparation of 3-methylene-1-oxa-5-thiacycloundecan-2-one (1b)

(a) Synthesis of α-(((6-hydroxyhexyl)thio)methyl)acrylic acid.

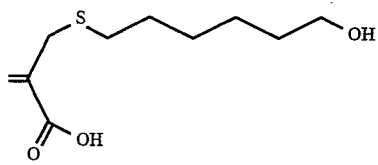

α-Bromomethylacrylic acid (2 g, 12.1 mmoles) was dissolved in 12 ml of dichloromethane and then 3.54 ml (2.57 g, 25.5 mmoles) of triethylamine was added dropwise at such a rate that boiling of the solution did not occur. After allowing the solution to stir for a few minutes, 1.79 g (13.0 mmoles) of 6-mercapto-1-hexanol was added to it. The flask was sealed and allowed to stir at room temperature overnight. The mixture was then poured into a solution of 10 ml of water, 20 ml of 2M sulfuric acid and 8 g of ammonium sulfate. After a few minutes a white precipitate formed. The solution was extracted with ether (3×20 ml). The extracts were dried and evaporated to give 1.5 g of white solid. The solid was recrystallised from toluene to give 1.3 g (50%) of the desired hydroxy acid.

$^1$H NMR (acetone-d$_6$): δ1.2–1.6 (8H, mult.), 2.38 (2H, t, 7 Hz, —S—CH$_2$—CH$_2$—), 3.22 (2H, s, allylic CH$_2$), 3.40 (2H, t 7H, —CH$_2$—O—), 5.60 (1H, s, =CH), 6.05 (1H, s. =CH).

$^{13}$C NMR (acetone-d$_6$): δ26.2, 29.3, 29.9, 31.8, 32.9, 33.4, 62.2 (—CH$_2$OH), 125.6 (=CH$_2$), 138.0 (quat, CH$_2$=C), 167.0 (C=O).

Mass spectrum (E.I.) m/z 218 (M$^+$60), 115 (100), 101 (62), 81 (75), 60 (55).

Mp. 72°–4° C.

(b) Cyclisation to 3-methylene-1-oxa-5-thiacycloundecan-2-one (1b).

A solution of 1.3 g (5.96 mmoles) of α-(((6-hydroxyhexyl)thio)methyl)acrylic acid and 6.63 ml (4.82 g, 47.7 mmoles, 8 molar equivalents) of triethylamine in 50 ml of dry dichloromethane was added by a mechanically driven syringe pump to a refluxing solution of 550 ml of dry dichloromethane containing 6.1 g (23.9 mmoles, 4 molar equivalents) of 2-chloro-1-methylpyridinium iodide over six hours.

After all the α-(((6-hydroxyhexyl)thio)methyl)acrylic acid solution had been added, the solution was further refluxed 40 minutes. The solution was filtered and the filtrate evaporated to give a viscous slurry. The slurry was taken up in water and extracted with dichloromethane (3×30 ml). The extracts were dried, evaporated to give 1.7 g of an orange oil. The oil was chromatographed on silica using dichloromethane as eluent to give 0.43 g (36% yield) of white solid.

$^1$H NMR (CDCl$_3$): δ1.45–1.85 (8H, mult, —(CH$_2$)$_4$—), 2.50 (2H, t, —CH$_2$—CH$_2$—S—), 3.30 (2H, s, allylic CH$_2$), 4.10 (2H, t, —OCH$_2$—), 5.40 (1H, s, vinylic H), 6.05 (1H, s, vinylic H).

$^{13}$C NMR (CDCl$_3$): δ22.5, 23.6, 23.9, 25.6 (all —(CH$_2$)$_4$—), 30.2 & 32.6 (both (—S—$_2$)), 66.1 (—O—CH$_2$—), 126.4 (=CH$_2$), 138.4 (quat. =C), 166.0 (C=O).

IR spectrum (thin film, CCl₄) 2933 m, 1724 s, 1631 w, 1439 w, 1303 s, 1233.5 m, 1189 s, 1132 m, 989 m, 948 m cm⁻¹.

Mass spectrum (E.I.) m/z 200 (M⁺, 100), 115 (65), 81 (41).

Mp. 59°–61° C.
$d^{25}$=1.138 g/cc

EXAMPLE 3

Preparation of 2-methyl-6-methylene-1,4-oxathiepan-7-one (2)

(a) Synthesis of α-(((2'-hydroxypropyl)thio)methyl)acrylic acid.

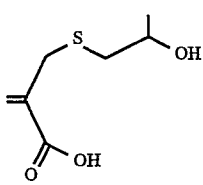

α-Bromomethylacrylic acid (5 g, 22.6 mmoles) was dissolved in 40 ml of dichloromethane cooled to ca. 10° C. under nitrogen and then 6.6 ml (4.8 g, 47 mmoles) of triethylamine was added dropwise at such a rate that boiling of the solution did not occur. After allowing the solution to stir for a few minutes, 2.2 g (24 mmoles) of 1-mercapto-2-propanol was added to it. The flask was sealed and allowed to stir at room temperature overnight. The mixture was then poured into a solution of 30 ml of water, 60 ml of 2M sulfuric acid and 24 g of ammonium sulfate. The mixture was vigorously extracted with ether. The extracts were dried and evaporated to give 4.5 g ( >100% yield) of white solid that smelt of mercaptan. The material was found to be difficult to purify and was used unpurified for further synthesis.

¹H NMR (CDCl₃): δ1.25 (3H, d, J=7.0 Hz, —(CH₃)), 2.46 (1H, dd, $J_{gem}$=13.9 Hz, $J_{vic}$ 8.5 Hz —SCH₂—CH(CH₃)OH), 2.65 ( dd, $J_{gem}$=13.9 Hz, $J_{vic}$=3.9 Hz —SCH₂—CH (CH₃)OH), 3.40 (2H, s, —CH₂S—), 3.9 (1H, br. mult., SCH₂CH(CH₃$_{OH}$), 5.70 (1H, s, vinylic H)., 6.15 (1H, s, vinylic H).

¹³C NMR (CDCl₃): δ23.9 (—CH₃), 34.5 (—SCH₂CH (CH₃)OH)), 42.5 ('CH₂S—), 683 (SCH₂CH(CH₃)OH), 130.3 (=CH₂), 138.4 (quat. =C), 172.1 (C=O).

(b) Cyclisation to 2-methyl-6-methylene-1,4-oxathiepan-7-one. (2)

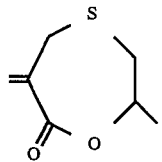

α-(((2-Hydroxypropyl)thio)methyl)acrylic acid was cyclised using the Mukaiyama method as described in Example 1 for 6-methylene-1,4-oxathiepan-7-one (1a). Two grammes (11.4 mmoles) of α-(((2-hydroxypropyl)thio)methyl)acrylic acid was cyclised and purified by column chromatography to give 1.1 g (60% yield) of the desired lactone.

¹H NMR (CDCl₃): δ1.45 (3H, d, J=6.5 Hz, —CH₃), 2.63 (2H, d, J=5.5 Hz, —SCH₂CH(CH₃)O—), 3.40 (2H, s, —CH₂S—), 4.61 (1H, mult, SCH₂CH(CH₃)O—), 5.52 (1H, s, vinylic), 5,82 (1H, s, vinylic).

¹³C NMR (CDCl₃): δ21.3 (—CH₃), 29.7 & 36.6 (both —CH₂S—), 76.4 (—OCH(CH₃)CH₂—), 123.8 (=CH₂), 142.4 (=C(CO)CH₂—), 170.1 (CO).

IR spectrum (thin film, CCl₄) 2948 w, 1735 s, 1559 w, 1294 m, 1235 m, 1171 m, 1117 m, 1033 m, 976 w, 938 w cm⁻¹.

Mass spectrum (CI, CH₄), m/z 159 (M⁺+1, 100%), 141 (90). Mass spectrum (HR, CI, CH₄) 159.0477 (C₇H₁₀O₂S+H requires 159.0480).

Mp 58°–60° C.
d=1.206 g/cc

EXAMPLE 4

Preparation of 9-methylene-1,4-dioxa-7-thiacyclodecan-10-one (3).

(a) Synthesis of α-(((5'-hydroxy-3'-oxa-pentyl)thio)methyl) acrylic acid.

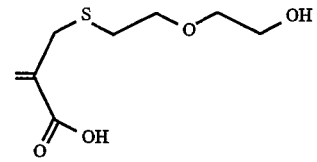

α-Bromomethylacrylic acid (5.2 g, 23.5 mmoles) was dissolved in 40 ml of dichloromethane cooled to ca. 10° C. under nitrogen and then 6.9 ml (5.0 g, 49.4 mmoles) of triethylamine was added dropwise at such a rate that boiling of the solution did not occur. Then 3 g (24.6 mmoles) of 2-(2-mercaptoethoxy)ethanol in 5 mls of dichloromethane was added dropwise to the solution. The solution was then allowed to warm to room temperature and stirred overnight. The reaction mixture was worked up by pouring the mixture into a solution of 24 g of ammonium sulphate, 30 ml of water and 60 ml of 2M sulfuric acid. The mixture was extracted with ether, the extracts dried and evaporated to give viscous oil which solidified to a wax. The wax was chromatographed on silica gel with ether but unknown vinylic impurities remained. The material was used subsequently without further attempts at purification. 1.4 g (yield ca. 30%) of material was obtained.

¹H NMR (CDCl₃): δ3.45 (2H, s, —SCH₂,(=CH₂)—), 3.6–3.8 (6H, malt, —CH₂O—), 5.0 (2H, br. s, OH), 5.8 (1H, s, vinylic), 6.35 (1H, s, vinylic).

¹³C NMR (CDCl₃): δ30.7 & 32.5 (both —SCH₂—), 61.2 (—CH₂OH), 70.1 & 71.9 (both —CH₂O—), 127.5 (=CH,), 136.6 (=C(CO)CH₂—), 168.5 (CO).

(b) Cyclisation to 9-methylene-1,4-dioxa-7-thiacyclodecan-10-one (3)

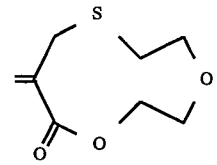

α-(((5-Hydroxy-3-oxa-pentyl)thio)methyl)acrylic acid was cyclised using the Mukaiyama method as described in Example 1 for 6-methylene-1,4-oxathiepan-7-one (1a). The crude α-(((5-Hydroxy-3-oxa-pentyl)thio)methyl)acrylic acid (1.4 g, 6.8 mmols) was cyclised and purified by column chromatography to give 400 mg (31% yield) of the desired lactone.

¹H NMR (CDCl₃): δ2.75 (2H, t, J=5.8 Hz, —SCH₂CH₂O—), 3.43 (2H, s,—SCH₂(=CH₂)—), 3.65 (2H, apparent q, J=ca. 5.7 Hz,—SCH₂CH₂OCH₂CH₂—), 4.40 (2H, apparent t, J=ca. 3Hz), 5.48 (1H, s, vinylic), 6.05 (1H, s, vinylic).

¹³C NMR (CDCl₃): δ34.3 & 34.4 (both —SCH₂—), 65.4 & 68.0 & 70.3 (all —OCH₂—), 125.7 (=CH₂), 139.5 (=C(CO)CH₂—), 166.6 (CO).

Mass spectrum (CI, $CH_4$) m/z 189 ($M^+$+1, 100%), 161 (25), 145 (15). Mass spectrum (HR, CI, $CH_4$) 189.0602 ($C_8H_{12}O_3S$+H requires 189.0585).

Mp 55°–7° C.

EXAMPLE 5

Preparation of 1,9-dioxa-3-methylene-5-thiacycloundodecan-2,8-dione (4)

(a) Synthesis of 4'-hydroxybutyl α-chloromethylacrylate.

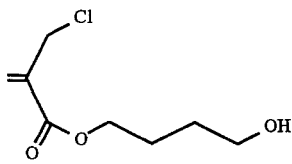

α-Chloromethylacrylchloride (10 g, 71.9 mmole) was added dropwise to mixture of 7.99 g (11.0 mmole of triethyl amine and 25.9 g (288 mmole) of 1,4-butandiol under nitrogen at 60° C. over 75 minutes. The reaction is exothermic and if the addition is started at 40° C., the exotherm will take the reaction temperature to the required 60° C. The solution was then allowed to stir under nitrogen for 2.5 hours, and during this time small crystals formed around the edge of the solution. The reaction mixture was worked up by pouring into 250 ml of water followed by vigorous extraction with ether. The ether extracts were dried and evaporated to give 8.2 g of pale yellow oil. Nmr spectroscopy on the sample showed it to consist of ca. 78% of the desired product and ca. 22% product due to disubstitution (4'-hydroxybutyl α-(4"-hydoxybutoxy)methylacrylate). The oil was chromatographed on silica with ether to give 5.5 g (43%) of clear oil. THIS COMPOUND IS STRONGLY SUSPECTED TO BE A VESICANT, IT SHOULD NOT BE ALLOWED TO COME IN CONTACT WITH SKIN.

$^1$H NMR ($CDCl_3$): δ1.4–1.8 (4H, mult, —$CH_2CH_2CH_2CH_2OH$), 2.5 (1H, s, OH), 3.55 (2H, t, J=7 Hz, —$CH_2OH$), 4.20 (2H, t, J=7 Hz, $COOCH_2$—), 4.25 (2H, s, —$CH_2Cl$), 5.85 (1H, s, vinylic), 6.30 (1H, s,vinylic).

$^{13}$C NMR ($CDCl_3$): δ25.0 & 28.0 (both —$CH_2CH_2CH_2CH_2OH$), 42.5 (—$CH_2Cl$), 62.0 & 65.0 (both —$CH_2O$—), 128.7 (=$CH_2$), 136.9 (=C(COOR)$CH_2$—), 165.0 (C=O).

(b) Synthesis of 4'-hydroxybutyl 2-methylene-4-thiaheptan-1,7-dioic acid C1 monoester.

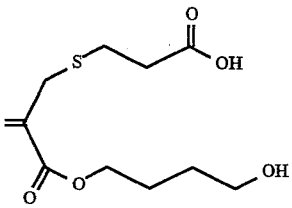

4-Hydroxybutyl chloromethylacrylate (5 g, 28.3 mmoles) was dissolved in 30 ml of dry dichloromethane. The solution was cooled and 8.8 ml (63.3 mmole) of dry triethylamine was added dropwise at such a rate that no boiling occurred. Then 3.3 g (31.1 mmoles) of 3-mercaptopropanoic acid on 8 ml of dichloromethane was added dropwise to the solution. The solution was allowed to reach room temperature and was stirred overnight. The reaction mixture was then poured into a mixture of 25 ml water, 75 ml of 2M sulfuric acid and 30 g of ammonium sulfate. The mixture was extracted with ether, the ether extracts dried and evaporated to give 7.4 g (106% yield) of clear oil. The oil was taken up in ether and washed with water to remove unreacted mercaptopropanoic acid. The ether was redried and evaporated to give 5.3 g (76%) of a clear oil.

$^1$H NMR ($CDCl_3$): δ1.6–1.8 (4H, mult,—$CH_2CH_2CH_2CH_2OH$), 2.4–2.8 (4H, mult, —$SCH_2CH_2CO$—), 3.35 (2H, s, =C(CO—)$CH_2S$—), 3.6 (2H, apparent t, J=ca7 Hz,—$OCH_2$—), 4.2 (2H, apparent t, J=ca 7 Hz, —$OCH_2$). 5.60 (1H, s,vinylic), 5.9 (ca 2H, br. s, —OH), 6.07 (1H, s, vinylic).

$^{13}$C NMR ($CDCl_3$): δ25.0, 26.2, 28.8, 32.9, 34.2, 62.0 & 64.9 (both —$CH_2O$—), 126.4 (=$CH_2$), 136.8 (=C(COOR)$CH_2$—), 166.3 (=C(COOR), 175.9 (—$CH_2COOH$).

(c) Cyclisation to 1,9-dioxa-3-methylene-5-thiacyclotridecan-2,8-dione. (4)

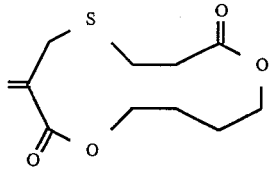

4'-Hydroxybutyl 2-methylene-4-thiaheptan-1,7-dioic acid C1 monoester was cyclised using the Mukaiyama method as described in Example 1 for 6-methylene-1,4-oxathiepan-7-one (1a). The crude 4'-hydroxybutyl 2-methylene-4-thiaheptan-1,7-dioic acid C1 monoester (2.7 g, 10.3 mmols) was cyclised and purified by column chromatography to give 1.4 g (55% yield) of the desired lactone. In this cyclisation, there was a side reaction of dimer formation (two hydroxy acids lactonising with each other to give a 26 membered ring). The amount can vary from almost none to ca 25%. This dimer was found to be inseparable from the mono lactone. The presence of this compound has no effect on the polymer chemistry as it fragments similarly to the mono lactone. When the oxidation of the monolactone was performed the two subsequently formed sulfones were found to be separable.

$^1$H NMR ($CDCl_3$): δ1.7–1.9 (4H, mult,—$CH_2CH_2CH_2CH_2O$—), 1.5 (2H, mult,—$SCH_2CH_2CO$), 1.7 (2H, mult,—$SCH_2CH_2CO$), 3.40 (2H, s., =C(CO—)$CH_2S$—), 4.05–4.20 (4H, mult, —$OCH_2$—), 5.55 (1H, s, vinylic), 6.05 (1H, s, vinylic).

$^{13}$C NMR ($CDCl_3$): δ25.1, 25.8, 28.2, 33.2 & 35.0 (both —$CH_2S$—), 64.1 & 64.7 (both —$OCH_2$—), 124.5 (=$CH_2$), 127.2 (=C(COOR)$CH_2$—), 166.0 (=C(COOR), 172.2 (—CH, COO—).

IR spectrum (thin film, $CCl_4$) 2943 m, 1728 m, 1630 m, 1302 s, 1189 s, 1133 s, 961 m. $cm^{-1}$.

Mass spectrum (EI) m/z 244 ($M^+$, 100%), 172 (55), 154 (85), 144 (33), 126 (31), 102 (25). Mass spectrum (HR, CI) m/z 245.0816 ($C_{11}H_{16}O_4S$+H requires 245.085)

$n_D^{20}$=1.520
$d^{25}$=1.236 g/cc

EXAMPLE 6

Preparation of 1,9-dioxa-3-methylene-5-sulfonocyclotridecan-2,8-dione (5).

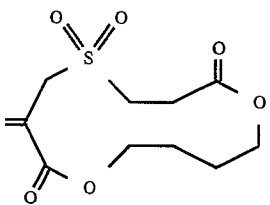

1,9-Dioxa-3-methylene-5-thiacyclotridecan-2,8-dione (1.3 g, 5.3 mmoles) was dissolved in 20 ml of methanol and cooled to 0° C. and a solution of 9.8 g of Oxone™ (DuPont) in 30 ml of water was slowly added. The reaction was then allowed to warm to room temperature and was stirred for 5 hours. The reaction mixture was worked up by pouring into 500 mls of water followed by vigorous extraction with dichloromethane. The dichloromethane extracts were dried and evaporated to give 1.4 g of white material. The material was chromatographed on silica with a solvent mixture of 80% dichloromethane and 20% tetrahydrofuran. The first fraction (tlc silica, rf=0.53) was collected and evaporated to give 450 mg of white powder of the desired product.

$^1$H NMR (CDCl$_3$): δ1.19 (4H, br.s, —CH$_2$CH$_2$CH$_2$CH$_2$O—), 2.90 (2H, apparent t., J=ca 7 Hz,—SO$_2$CH$_2$CH$_2$CO), 3.50 (2H, apparent t., J=ca 7 Hz,—SO$_2$CH$_2$CH$_2$CO), 4.12 (2H, s, =C(CO—)CH$_2$SO$_2$—), 4.30 (4H, mult, —OCH$_2$), 6.05 (1H, s, vinylic), 6.65 (1H, s, vinylic).

$^{13}$C NMR (CDCl$_3$): δ24.2, 24.6, 29.3, 49.7, & 55.7 (both —CH$_2$S—), 65.0 & 65.1 (both —OCH$_2$—), 127.8 (=CH$_2$), 134.6 (=C(COOR)CH$_2$—), 164.5 & 170.5 (C=O).

Mass spectrum (CI, CH$_4$) m/z 277 (M$^+$+1, 100%), 213 (25), 205 (35), 141 (30), 127 (30), 91 (25). Mass spectrum (CI, HR) 277.0739 (C$_{11}$H$_{16}$O$_6$S+H requires 277.0746).

Mp 127°–9° C.

The second fraction (tlc silica, rf=0.36) was collected and evaporated to give 50 mg of a white crystalline material which was identified as the 26-membered ring dimer of 1,9-dioxa-3-methylene-5-sulfonocyclotridecan-2,8-dione.

$^1$H NMR (CDCl$_3$): δ1.17 (4H, br. s, —CH$_2$CH$_2$CH$_2$CH$_2$O—), 2.80 (2H, t., J=7 Hz,—SO$_2$CH$_2$CH$_2$CO), 3.35 (2H, t., J=7 Hz,—SO$_2$CH$_2$CH$_2$CO), 4.0 (2H, s, =C(CO—)CH$_2$SO$_2$—), 4.12 (4H, t, J=5.8 Hz —OCH$_2$—), 4.22 (4H, t, J=6.0 Hz —OCH$_2$—), 6.10 (1H, s, vinylic), 6.55 (1H, s, vinylic).

$^{13}$C NMR (CDCl$_3$): δ25.0, 25.1, 27.2, 48.1, & 54.9 (both —CH$_2$SO—), 64.6 & 65.2 (both —OCH$_2$—), 127.4 (=CH,), 134.4 (=C(COOR)CH$_2$—), 165.2 & 170.2 (C=O).

Mass spectrum unobtainable.

Mp 142°–5° C. with decomposition.

EXAMPLE 7

Preparation of 5-methyl-6-methylene-1,4-oxathiepan-7-one (6).

(a) Synthesis of t-butyl Z-2-(bromomethyl)but-2-enoate.

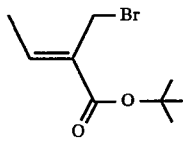

t-Butyl 3-hydroxy-2-methylenebutanoate (10 g, 58.1 mmoles) was dissolved in 100 ml of dry ether and cooled to −10° C. under nitrogen. Then 2.7 ml (29.1 mmole, 7.8 g) of phosphorus tribromide was added dropwise over 20 minutes. The reaction was then allowed to warm to room temperature and was stirred for a further 2 hours. The solution was then recooled to ca 10° C. and 100 ml of water was cautiously added. The mixture was extracted with ether, the extracts were washed with brine, dried (MgSO$_4$) and evaporated to give 11.0 g (80% yield) of clear oil. This was essentially pure t-butyl Z-2-(bromomethyl)but-2-enoate and was used without further purification.

$^1$H NMR (CDCl$_3$): δ1.45 (9H, s, t-butyl), 1.85 (3H, d, J=7.1 Hz, =CHCH$_3$), 4.19 (2H, s, —CH$_2$Br), 6.93 (1H, q, J =7.1 Hz, vinylic).

$^{13}$C NMR (CDCl$_3$): δ14.4 (=CHCH,), 24.4 (—CH$_2$Br), 28.0 (—CH$_3$), 81.0 —C(CH$_3$)$_3$), 131.6 (quatern. vinylic), 141.8 (=CHCH$_3$), 164.6 (C=O).

IR spectrum (neat, thin film) 2977 m, 1711 s, 1368 m, 1291 s, 1255 m, 1217 m, 1154 vs. 847 w, 766w cm$^{-1}$.

n$_D^{20}$=1.4747

(b) Synthesis of Z-2-(bromomethyl)but-2-enoic acid

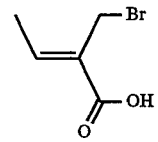

t-Butyl Z-2-(bromomethyl)butenoate (8 g, 34.0 mmoles) was added to 20 ml of 10M sulfuric acid at room temperature with vigorous stirring. After a few minutes (ca 10–15 mins) the two phase solution changed colour to light brown/orange. After about 4 hours tlc showed that no ester remained. A precipitate had now formed in the solution. The mixture was extracted with dichloromethane, the extracts were dried and evaporated to give 5.7 g (ca 95%) of brown solid. The solid was then chromatographed on silica with ether. The appropriate fractions were combined and evaporated to give 4 g (67%) of white powder.

$^1$H NMR (CDCl$_3$): δ1.95 (3H, d, J=7.3 Hz, —CH$_3$), 4.15 (2H, s, —CH$_2$Br) 7.15 (1H, q, J=7.3 Hz, vinylic), 11.6 (1H, s, OH).

$^{13}$C NMR (CDCl$_3$): δ14.9 (=CHCH$_3$), 23.4 (—CH$_2$Br), 129.8 (quatern. vinylic), 146.3 (=CHCH$_3$), 171.3 (C=O).

Mass Spectrum (CI, CH$_4$). m/z 181 (M$^+$+1, 90%), 179 (M$^+$+1, 100), 163 (20), 161 (25), 127 (20), 101 (40), 100 (40), 99 (74). Mass Spectrum (CI, HR) 178.9690 (C$_5$H$_8$O$_2$Br+H requires 178.9708).

Mp 106°–7° C.

(c) Synthesis of 2-methylene-3-((2'-hydroxyethyl)thio) butanoic acid.

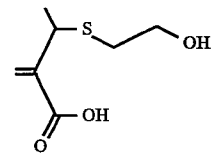

Z-2-(Bromomethyl)but-2-enoic acid (3.5 g, 19.6 mmole) was dissolved in 20 ml of dichloromethane and cooled with ice under a nitrogen atmosphere. Then 5.7 ml (4.1.1 mmole, 4.15 g) of triethyl amine was added cautiously such that the solution temperature remained ca 10° C. After a few minutes a solution of 1.6g (20.6 mmole) of mercaptoethanol in 5 ml of dichloromethane was added slowly over 10–15 minutes. The reaction was allowed to stir overnight at room temperature. The reaction mixture was then poured into a mixture of 30 ml of water, 4 ml of 10M sulfuric acid, and 10 g of ammonium sulfate. This was then extracted with ether. The extracts were dried and evaporated to give 3.2 g of yellowish oil. $^1$H NMR showed that it was essentially the desired product with a trace amount (ca 5%) of the unrearranged material. The oil was chromatographed on silica with ether. The appropriate fraction were combined and evaporated to give 1.6 g (43%) of clear oil.

$^1$H NMR (CDCl$_3$): δ1.45 (3H, d, J=7 Hz, —CH$_3$), 2.65 (2H, apparent t. J=ca. 5 Hz, —CH$_2$OH), 3.7 (2H, mult., —CH$_2$S—), 3.9 (1H, q, J=7.0 Hz), 5.7 (ca 2H, br.s, —OH), 5.75 (1H, s, vinylic), 6.25 (1H, s, vinylic).

$^{13}$C NMR (CDCl$_3$) (DEPT (+) CH, CH$_3$; (−) CH$_2$): δ20.7 (—CHCH$_3$, +), 33.9 (—CH$_2$S—,—), 38.5 (—CHS—, +), 61.0 (—CH$_2$O,—), 126.0 (=CH$_2$—), 141.8 (quat. vinylic), 170.2 (CO).

(d) Cyclisation to 5-methyl-6-methylene-1,4-oxathiepan-7-one.

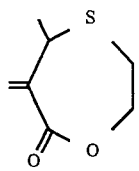

2-Methylene-3-((2'-hydroxyethyl)thio)butanoic acid was cyclised using the Mukaiyama method as described for 6-methylene-1,4-oxathiepan-7-one (1a). The 2-methylene-3-((2'-hydroxyethyl)thio)butanoic acid (1.5 g, 8.5 mmols) was cyclised and purified by column chromatography to give 0.7 g (52% yield) of the desired lactone.

$^1$H NMR (CDCl$_3$): δ1.40 (3H, d, J=7.1 Hz, —CH$_3$), 2.85 (2H, apparent q, J=ca 5 Hz, —SCH$_2$—), 3.50 (1H, q, J=7,1 Hz, (—CH), 4.40 (2H, apparent t, J=ca 5 Hz, —OCH$_2$—), 5.40 (1H, s, vinylic), 5.50 (1H, s, vinylic).

$^{13}$C NMR (CDCl$_3$): δ19.5 (—CH$_3$), 29.4 & 37.2 (both —C(H or H$_2$)S—), 70.3 (—OCH$_2$—), 120.0 (=CH$_2$), 147.7 (quat. vinylic), 171.5 (C=O).

IR spectrum (neat, thin film) 2953 m, 1728 s, 1452 m, 1406 m, 1309 s, 1138 s, 1050 m, 1014 m, 935 m cm$^{-1}$.

Mass spectrum (CI, CH$_4$). m/z 159 (M$^+$+1, 100%), 99 (20), Mass spectrum (CI, HR) 159.0488 (C$_7$H$_{10}$O$_2$S+H requires 159.0480)

$n_D{}^{20}$=1.5332.

EXAMPLE 8

The Polymerisation Chemistry of Compounds of Formula 1.

(a) Preparation of Copolymers of Methyl Methacrylate and 1a

A 1 ml solution of azobisisobutyronitrile (0.05M, 8.2 mg), lactone 1a (0.5M, 72.0 mg), inhibitor-free methyl methacrylate (2.5M, 250.2 mg) and non-deuterated benzene (0.63M, 48.5 mg) in benzene-d$_6$ was prepared. A sample of ca. 0.6 ml was placed in an NMR tube, freeze-thaw degassed under vacuum, and sealed. The sample was polymerised at 70° C. for five hours and the extent of polymerisation was monitored by $^1$H NMR spectroscopy. During this time, both monomers were consumed at the same rate and signals grew at δ6.3 (1H, =CH), 5.2–3 (1H, =CH) and 4.15 (2H, —OCH$_2$—) due to the formation of the acrylate segment (see Scheme 1) of the copolymer backbone grew (evidence of ring opening of 1a). At the end of the polymerisation, the $^1$H NMR showed conversion of methyl methacrylate was 95.2% and lactone 1a was 94.2%. A small portion of the contents of the NMR robe was examined by gel permeation chromatography (GPC) using a Waters Instrument connected to six μ-Styragel columns (10$^6$, 10$^5$, 10$^4$, 10$^3$, 500, and 100 Å pore size) Tetrahydrofuran was used as eluent at a flow of 1 ml/min and the system was calibrated using narrow distribution polystyrene standards (Waters). Number average weight was 6899, weight average molecular weight was 22388, and the polydispersity was 3.24.

The remaining contents of the NMR tube were poured into methanol and the precipitated copolymer was collected and freeze dried. The copolymer was analysed by $^1$H and $^{13}$C NMR spectroscopy. The ratio of ring opened monomer to methyl methacrylate in the polymer was 1:5.6. Ring opening of 1a was complete and the repeating unit due to 1a was clearly and unambiguously identified (see below for NMR spectral assignments C=$^{13}$C, H=$^1$H, in ppm. (CDCl$_3$)) in the copolymer.

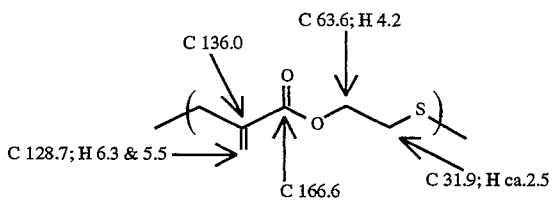

(b)

Table 1 shows the utility of the monomers of formula 1 to undergo copolymerisation with methyl methacrylate. Note that in most cases the ratio of compound: MMA in the monomer feed results in a copolymer of essentially the same composition. This suggests that the reactivity ratio of the compounds and MMA are both near to, or actually 1.0.

TABLE 1

| | Copolymers with Methyl Methacrylate | | | | | |
|---|---|---|---|---|---|---|
| | $^1$H NMR signals due to ring opened monomer (ppm)$^a$ | | Ratio of compound: MMA in copolymer$^{b,c}$ | $M_w{}^d$ | Dispersity$^d$ | Conversion (%)$^b$ |
| Compound | Vinylic | —OCH$_2$— | | | | |
| 1a | 6.3, 5.3 | 4.1 | 1:5.6 | 25 000 | 2.5 | 90 |
| 1b | 6.2, 5.3–5 | 4.1 | 1:5 | 34 000 | 5.0 | 80 |
| 2 | 6.2, 5.4–6 | 4.9 | 1:5 | 18 000 | 4.6 | 85 |
| 3 | 6.2, 5.5 | 4.3 | 1:5 | 40 000 | 7.9 | 80 |
| 4 | 6.1, 5.3–5 | 4.1 | 1:5.6 | 36 500 | 3.9 | ca. 80 |
| 6 | 6.9 | 4.2 | 1:10 | 19 000 | 1.9 | 80 |

$^a$NMR spectra of precipitated, freeze dried polymer, CDCl$_3$ used as solvent.
$^b$Determined from NMR.
$^c$Initial ratio of compound: MMA was 1:5 in benzene as described above in all cases.
$^d$Determined on polymerisation solution before precipitation and freeze drying.

(c)

Table 2 shows the utility of compounds of formula 1 (using compound 1a) to homo and co-polymerise with other monomers. Note the cross linking that occurs with mono substituted activated ethylene monomers (sty and MA).

TABLE 2

The Homo and Co polymers of Compound 1a.

| Monomer/ comonomer | $^1$H NMR signals due to ring opened monomer (ppm)[a] | | Ratio of compound: comonomer in copolymer[b,c] | $M_w^d$ | Dispersity[d] | Conversion (%)[b] |
|---|---|---|---|---|---|---|
| | Vinylic | —OCH$_2$— | | | | |
| homopol.[f] | 6.4, 5.6 | 4.2 | n/a | 112 000 | 5.5 | ca 50 |
| MMA (1:5) | 6.3, 5.3 | 4.1 | 1:5.6 | 25 000 | 2.5 | 90 |
| MMA (1:1)[e] | 6.3, 5.7, 5.5 | 4.1 | 1:1 | n/o | | 90 |
| MAN | 6.4, 5.9 | 4.2 | 1:6.7 (est) | 4100 | 1.8 | 50 |
| Styrene | | | insoluble cross linked gel formed | | | |
| MA | | | insoluble crosslinked gel formed | | | |

[a]NMR spectra of precipitated, freeze dried polymer, CDCl$_3$ used as solvent.
[b]Determined from NMR.
[c]Initial ratio of compound:Comonomer was 1:5 in benzene as describe above in all cases.
[d]Determined on polymerisation solution before precipitation and freeze drying.
[e]Sample gelled at 90% conversion. Reported Vinylic and alkoxy protons are from benzene solution.
[f]For bulk or solution polymerisation carried out with continuous heating, a cross linked, insoluble polymer formed.

(d)
Table 3 shows the advantage of alpha substituents on compounds of formula 1 (as illustrated with compound 6). The substituent allows the monomer to homopolymerise and copolymerise with mono substituted activated ethylene monomers (sty and MA) without cross linking occuring. This is due to the deactivation (steric and/or electronic) of the new double bond formed from the ring opening process.

TABLE 3

Homo and Co Polymers with Compound 6

| Compound | $^1$H NMR signals due to ring opened monomer (ppm)[a] | | Ratio of compound: comonomer in copolymer[b,c] | $M_w^d$ | Dispersity[d] | Conversion (%)[b] |
|---|---|---|---|---|---|---|
| | Vinylic | —OCH$_2$— | | | | |
| homopol. | 6.9 | 4.3 | n/a | 46 200 | 2.3 | 82 |
| MMA | 6.9 | 4.2 | 1:10 | 19 200 | 1.9 | 90 |
| Styrene | n.o. | 4.0 | 1:8 | 17 100 | 1.8 | (70+ |

[a]NMR spectra of precipitated, freeze dried polymer, CDCl$_3$ used as solvent. (except for homo polymer where the solvent was benzene)
[b]Determined from NMR.
[c]Initial ratio of compound:comonomer was 1:5 in benzene as described above in all cases.
[d]Determined on polymerisation solution before precipitation and freeze drying.

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

We claim:

1. Compounds of the Formula 1

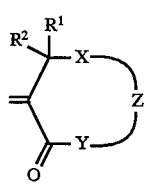

Formula 1 wherein:

R and R$^2$ are independently selected from the group comprising hydrogen, C$_1$ to C$_6$ alkyl, C$_1$ to C$_6$ haloalkyl, phenyl, and substituted phenyl;

X is sulfur;
Y is oxygen; and
Z is any linking functionality.

2. Compounds as claimed in claim 1, characterised in that Z is —(CWT)$_n$—O—(CO)—O—(CWT)$_m$—, —(CWT)$_n$—, —(CWT)$_n$—O—(CO)—(CWT)$_m$—, —(CWT)$_n$—O—(CWT)$_m$—, —(CWT)$_n$—CO—(CWT)$_m$—, —(CWT)$_n$—(C=O)—, —(CWT)$_n$—S—(CWT)$_m$—, —(CWT)$_n$—S—(CWT)$_m$—, —(O—CWTCWT)$_n$—, phenylene, or substituted phenylene, wherein W, T are independently selected from hydrogen, C$_1$ to C$_6$ alkyl, C$_1$ to C$_6$ haloalkyl, phenyl, substituted phenyl or halogen and m,n are whole numbers).

3. Compounds as claimed in claim 1, characterised in that the ring system in Formula 1 contains from 6 to 50 atoms.

4. Any one of the following compounds:

6-methylene-1,4-oxathiepan-7-one;

3-methylene-1-oxa-5-thiacycloundecan-2-one;

2-methyl-6-methylene-1,4-oxathiepan-7-one;

9-methylene-1,4-dioxa-7-thiacyclodecan-10-one;

1,9-dioxa-3-methylene-5-thiacycloundodecan-2,8-dione;

1,9-dioxa-3-methylene-5-sulfonocyclotridecan-2,8-dione; or 5-methyl-6-methylene-1,4-oxathiepan-7-one.

5. A polymerisation process characterised in that it comprises the free radical polymerisation of a compound as claimed in claim 1.

6. A process as claimed in claim 5, characterised in that the free radical polymerisation is carried out in the presence of at least one comonomer.

7. A process as claimed in claim 5, characterised in that the comonomer is selected from the group comprising acrylates, methacrylates, acrylonitriles, methacrylonitriles and styrenes.

8. A polymer or copolymer characterised in that it comprises repeating units of Formula 2.

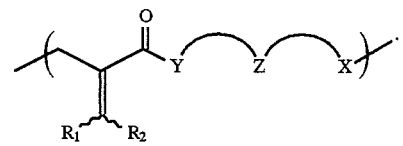

Formula 2

9. Polymers made by the polymerisation process claimed in claim 5.

* * * * *

UNITED STATES PATENT AND TRADEMARK OFFICE
CERTIFICATE OF CORRECTION

PATENT NO. : 5,665,839

DATED : September 9, 1997

INVENTOR(S) : RIZZARDO et al.

It is certified that error appears in the above-identified patent and that said Letters Patent is hereby corrected as shown below:

Column 2, line 50 should read:
  with $R^1 = R^2 = H$; $X = S$; $Z = -CH_2CH_2-$; $Y = O$.

Column 3, line 32, the parenthetical phrase should read:
  (for compounds where $R^1 = R^2 = H$)
line 52, the partial parenthetical phrase should read:
  $R^1 = R^2 = H$).
line 61, the definitions $R^1$ and $R^2$ should read:
  $R^1 = R^2 = H$ Column 4, line 4, the partial parenthetical phrase should read:
  (e.g. $R^1 = H$,
line 5, the partial parenthetical phrase should read:
  $R^2 = CH_3$, i.e. compound 6 below),
line 16, the partial parenthetical phrase should read:
  ($R^1 = H$,
line 17, the partial parenthetical phrase should read:
  $R^2 = CH_3$)

UNITED STATES PATENT AND TRADEMARK OFFICE
CERTIFICATE OF CORRECTION

| | |
|---|---|
| PATENT NO. : 5,665,839 | |
| DATED : September 9, 1997 | |
| INVENTOR(S) : RIZZARDO et al. | |

It is certified that error appears in the above-identified patent and that said Letters Patent is hereby corrected as shown below:

Column 14, line 20, the definitions for C and H should read:

$$C = {}^{13}C, H = {}^{1}H$$

Column 15, line 65, "Rand $R^2$" should read --$R^1$ and $R^2$--.

Signed and Sealed this

Twenty-eighth Day of April, 1998

*Attest:*

BRUCE LEHMAN

*Attesting Officer*  Commissioner of Patents and Trademarks